United States Patent [19]

Ryder et al.

[11] Patent Number: 4,492,854

[45] Date of Patent: Jan. 8, 1985

[54] CONTACT LENS DISINFECTOR

[75] Inventors: Francis E. Ryder; Scott Ryder, both of Arab, Ala.

[73] Assignee: Ryder International Corporation, Arab, Ala.

[21] Appl. No.: 552,170

[22] Filed: Nov. 15, 1983

[51] Int. Cl.[3] .......................... A61L 2/04; H05B 1/02

[52] U.S. Cl. .......................... 219/521; 219/386; 219/439; 219/505; 219/530; 338/22 R; 422/307

[58] Field of Search .............. 219/386, 438, 439, 441, 219/504, 505, 521, 530; 422/105, 301, 307; 338/22 R, 22 SD

[56] References Cited

U.S. PATENT DOCUMENTS

| | | | |
|---|---|---|---|
| 3,801,278 | 4/1974 | Wagner et al. | 219/439 X |
| 4,165,359 | 8/1979 | Thomas et al. | 422/105 |
| 4,302,664 | 11/1981 | Ryder et al. | 219/504 |
| 4,303,828 | 12/1981 | Thomas et al. | 219/521 |
| 4,331,859 | 5/1982 | Thomas et al. | 219/521 |
| 4,371,777 | 2/1983 | Roller et al. | 219/505 X |
| 4,379,965 | 4/1983 | Dounce et al. | 219/521 |
| 4,388,521 | 6/1983 | Thomas et al. | 219/521 |

*Primary Examiner*—Volodymyr Y. Mayewsky
*Attorney, Agent, or Firm*—Trexler, Bushnell & Wolters, Ltd.

[57] ABSTRACT

A contact lens disinfector has a pair of wells that are axially aligned and open in opposite directions from the disinfector casing. Between the wells is a positive temperature coefficient thermistor which serves as a heater to supply heat through a pair of heat sinks on opposite sides of the heater. Each heat sink has a spherically curved surface which engages flush with a companion shaped wall of the lens well to enhance the transfer of heat from the heater to the solution within the lens well.

11 Claims, 5 Drawing Figures

20
8
18
2
35
20

20
6

38
36
3
28
26
44
42
22
46
40
41
30
28
36
32
34
32
34
35
13
15
24
48
43
14
4
20

50
34
26
34

20
18
8
6
13
38
12
28
15
15
14
41
3
3
30
43
35
16
24
26
38
12
28
42
4
2
22
36
18
10
20

50
34
32
44
30
14
48
24
46
35
34

CONTACT LENS DISINFECTOR

BACKGROUND OF THE INVENTION

This invention relates to disinfectors for contact lenses and the like.

In order to prevent or reduce the possibility of eye infection, soft contact lenses must be subject to a disinfecting action periodically. In order to accomplish this, the lenses are heated to a sufficient temperature for a specified length of time in the disinfector. Many disinfector units are designed to heat the lenses rather quickly, but this has been found to be somewhat unsatisfactory because the high temperature short time process tends to deteriorate the lenses. Actually, the preferred disinfecting procedure is one wherein a lower temperature is used for a longer period of time, and a preferred procedure is to utilize a disinfecting cycle in which the temperature is in the range of 60 degrees Centigrade-80 degrees Centigrade.

OBJECTS AND SUMMARY OF THE INVENTION

An object of this invention is to provide a contact lens disinfector in which the temperature of the saline solution used for disinfecting is rather carefully controlled to avoid deterioration of the lenses as far as their transparency is concerned.

An additional object of this invention is to provide a disinfector of the type stated which is relatively compact and is of low cost construction whereby the unit may be carried in a purse or coat pocket with relative ease.

A still further object of this invention is to provide a disinfector of the type stated in which the contact lens wells are aligned but are back-to-back and with the heater disposed therebetween and with a heat sink construction designed to cooperate with the lens well so as to provide a high rate of heat transfer from the heater to the lens well and to the disinfecting solution therein.

A still further object of this invention is to provide a disinfector of the type stated which utilizes as its heater element a positive temperature coefficient (PTC) thermistor. A heater of this type has an electrical resistance that increases upon increases of temperature above a predetermined temperature, thereby to limit the maximum operating temperature of the heater. The aforesaid predetermined temperature is that temperature at which the resistance begins to increase rapidly in response to small temperature rises, and is referred to as the switching temperature of the thermistor. The thermistor heater thus has an extremely large resistance change in a small temperature span. Thermistors of this type are known and are commercially available, and therefore they need not be described in detail herein.

In accordance with the foregoing objects, the contact lens disinfector comprises a casing having a pair of wells at opposite ends thereof and opening in opposite directions for receiving contact lenses and a quantity of disinfecting solution, each well opening to an end surface of the casing, and removable cover means overlying the associated well opening, each said well having an end wall opposite to said end surface, a pair of metallic heat sink elements in said casing exterior of each said wells and each heat sink element having a surface disposed against an associated end wall in intimate surface-to-surface contact therewith, electrical heater means intermediate said heat sink elements for supplying heat in opposite directions to each heat sink element, said heater means being of the type having an electrical resistance that increases upon increases of temperature above a predetermined temperature to limit the maximum operating temperature of the heater means, electrical contacts on opposite sides of said heater means and being in electrical circuit-forming relation with said heater means, an insulator between said contact means, and power supply leads connected to said contacts and extending therefrom to the exterior of said casing for connection to a source of power.

In an embodiment of the invention shown, each well has an arcuately shaped end wall of spherical configuration and the associated metallic heat sink element in contact therewith has a surface of like configuration whereby to enhance the transfer of heat from the heater to the well.

DETAILED DESCRIPTION

Figure 3:
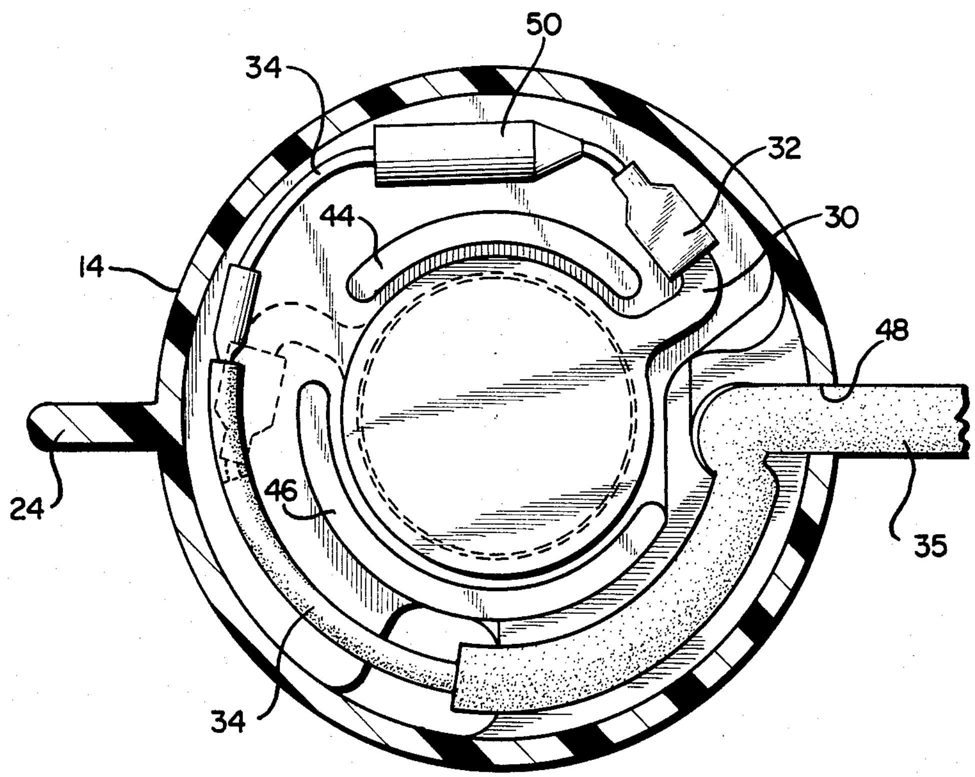
FIG. 3 is a sectional view taken along line 3—3 of FIG. 2.

Referring now in more detail to the drawing, there is shown a plastic casing or housing 2, comprised of sections 4, 6 which are telescoped together to form the assembled casing 2. Lens wells 8, 10 are formed on the respective casing sections 4, 6, and in the assembled unit the lens wells are coaxial and back-to-back and with there being an interior space or cavity therebetween. Each lens well has an end wall 12, FIG. 3, with a spherically contoured convex outer surface 13. The walls 12, 12 cooperate with outer flange portions 14, 16 at which the contact sections 4, 6 are assembled to form a cavity 15 within the casing 2. The lens wells 8, 10 open in opposite directions and have peripheral walls 18, 18 which are externally threaded for receiving removable closure caps 20, 20. One of the casing sections 4 may have a radial flange or rib 24 that constitutes a handle for holding the heated casing, or provides means for affixing a lable to the casing or housing 2.

Interposed between the end walls 12, 12 and within the cavity 15 is a heater arrangement designated generally 22. The heater arrangement 22 includes a PTC heater 26 of the type heretofore described. The PTC heater 26 is of generally cylindrical configuration and is coaxial with the end walls 12, 12. Conventionally, the opposite sides of the heater 26 are formed with or constitute contacts providing electrical connections to the heater 26. In the form of the invention herein shown, there is provided a pair of metal disc contacts 28, 28 positioned on opposite sides of the heater 26 and which are flush against the sides of the heater. These contacts are of generally circular configuration and include ears 30 for receiving spade terminals 32, 32 which are at the ends of power supply leads 34, 34, the latter being adapted for connection to a source of electric power.

Disposed against the contacts 28, 28, and intermediate said contacts and the end wall surface 13, are heat sinks 36, 36 of a high heat conductive material such as aluminum. Each heat sink 36, 36 has a flat side which is in surface-to-surface engagement with the associated contact 28, 28 and an opposite side 38, 38 of a spherically concaved configuration matching that of the exterior surface 13 of the associated wall 12 and being flush thereagainst. Such an arrangement enhances the transfer of heat from the heater 26 to the discs 28, the heat sink 36 and through the wall 12 to the lens wells 8, 10.

Figure 1:
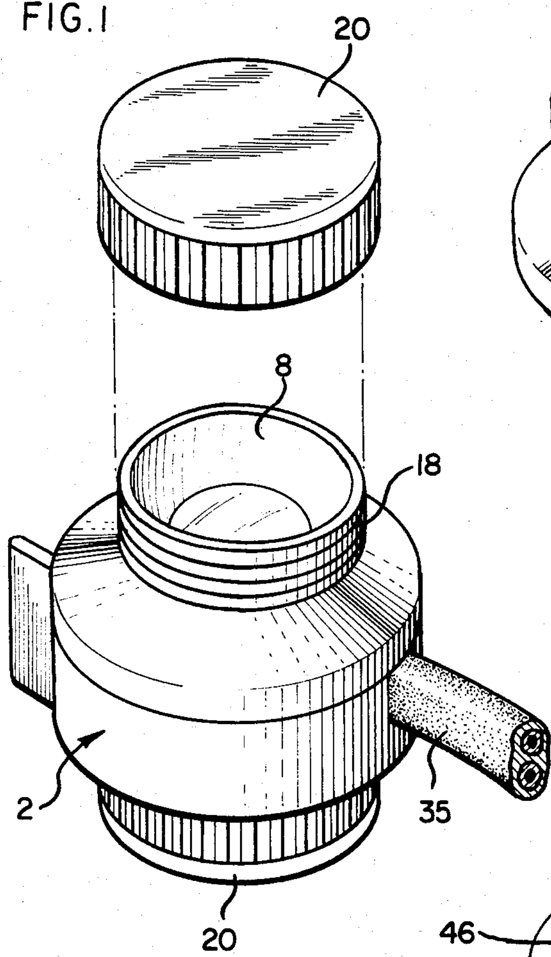
FIG. 1 is a perspective view of a disinfector shown partially exploded to the extent of illustrating the device with one of the well caps being removed.
Figure 4:
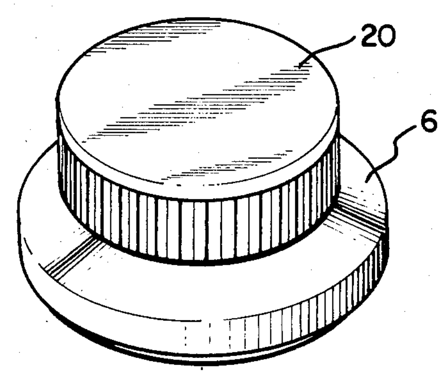
FIG. 4 is an exploded perspective view of the disinfector.
Figure 4:
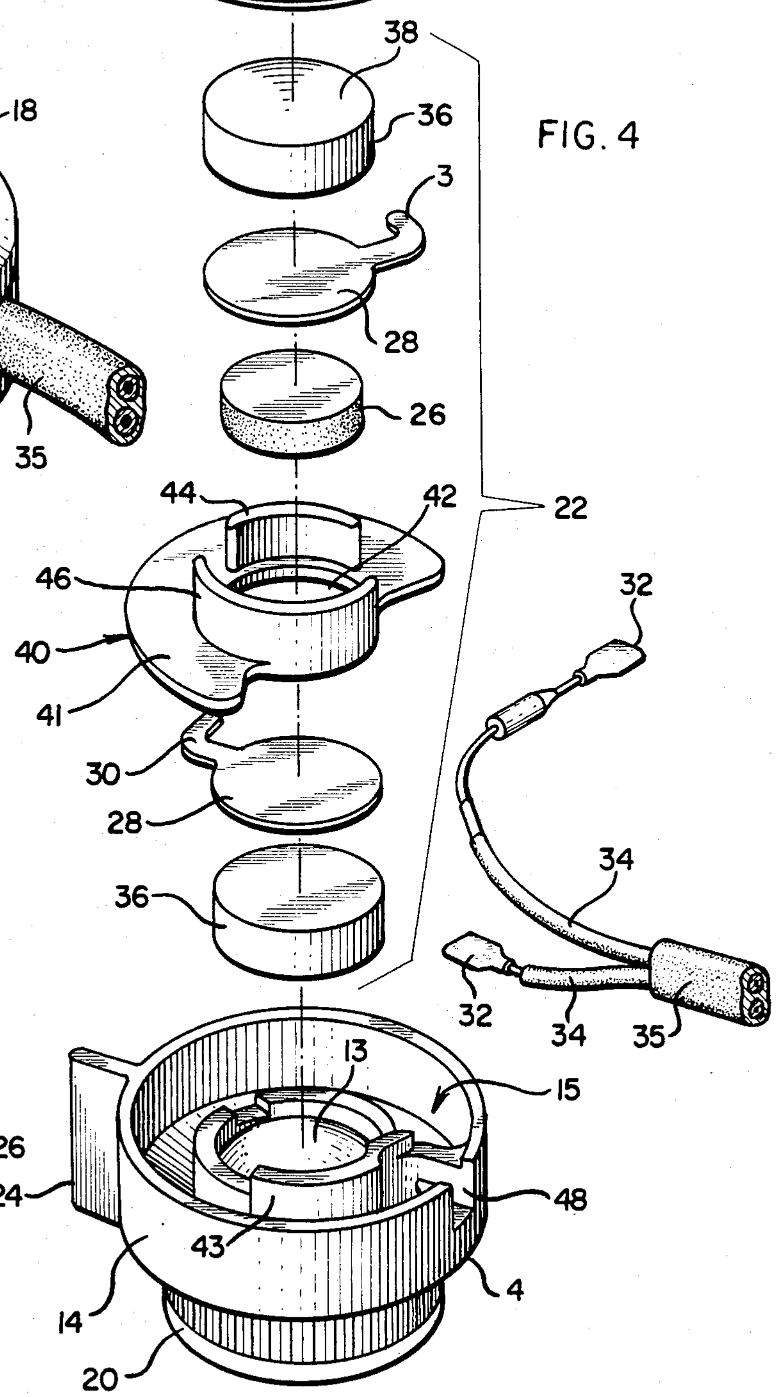

Within the chamber 15 is an insulator 40 having a central aperture 42, see FIG. 4, through which the PTC heater 28 projects. The insulator 40 is also formed with a radial flange 41 and circumferentially spaced axial flanges 44, 46 which surround the aperture 42 and between which one of the ears 30 projects for connection with its associated spade terminal 32. The casing section 4 has an annular wall 43 which receives one of the heat sinks 36 and the ear 30 of the associated contact 28. The flanges 41, 44, 46 and the wall 43 serve to insulate the ears 30 and the terminals 32 on the power leads 34, 34 from short circuiting with the PTC heater 26, and the insulator 40 also serves to prevent short circuiting of the opposed contacts 28, 28. Power supply leads 34, 34 are themselves insulated and also are part of the line cord 35 that projects through an opening 48 that is formed by the assembled casing sections 4, 6.

Figure 5:
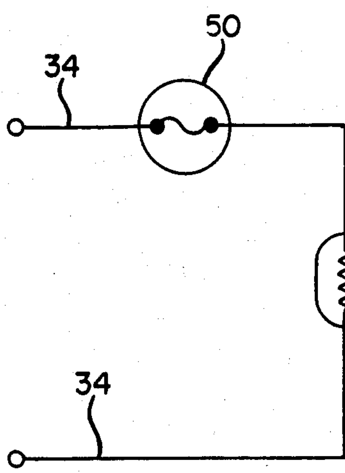
FIG. 5 is a partial circuit diagram of a circuit used in the disinfector.
Figure 2:
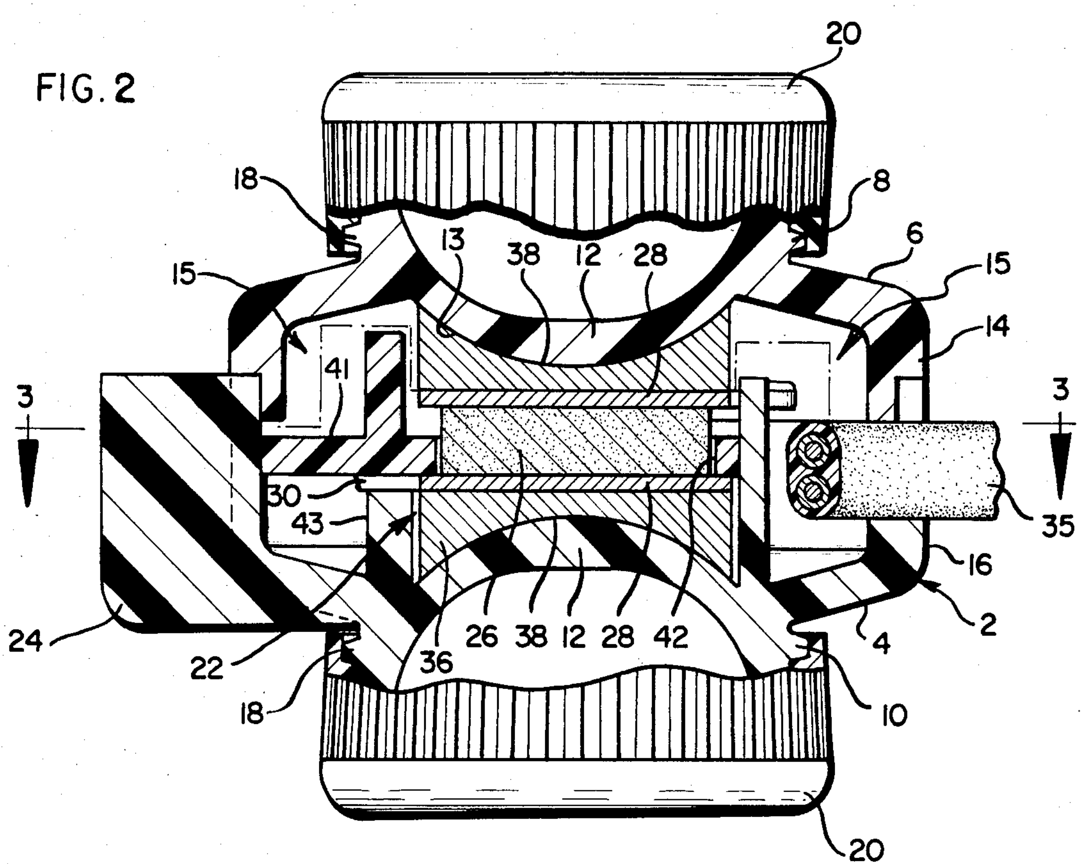
FIG. 2 is a partial sectional view of the disinfector taken through the central axis of the disinfector.

As shown in FIG. 5, the circuit for the unit may comprise a thermal cutoff 50 which serves to interrupt the circuit to the heater 26 should the heater arrangement 22 overheat as a result of the drawing of excessive current.

In use, the wells 8, 10 are filled with the disinfecting solution and the contact lens is deposited in the wells. The caps are threaded on to the walls 18, 18. The heater 26 is then activated to increase the temperature of the disinfecting solution to about 60 degrees Centigrade-80 degrees Centigrade. This temperature is maintained for a considerable period of time in order to attain the proper disinfecting action.

While a preferred form of the invention has been illustrated and described, it is envisioned that those skilled in this art may devise various alternatives or modifications once possessed of a disclosure of the invention. As such, it is intended that the spirit and scope of the invention be defined by the claims appended hereto, and not limited to the specific disclosed embodiment.

The invention is claimed as follows:

1. A contact lens disinfector comprising: a casing formed from an electrically insulative material and defining a pair of wells at opposite ends thereof for receiving contact lenses and a quantity of disinfecting solution, each well opening to an end surface of the casing, and removable cover means attachable to said casing at each end thereof to overlie the associated well opening, each said well having an arcuately shaped end wall opposite to said end surface, a pair of metallic heat sink elements in said casing exterior of said wells and each heat sink element having a surface disposed against an associated end wall surface, electrical heater means intermediate said heat sink elements and in heat conductive engagement with said heat sink elements for supplying heat to each heat sink element, said heater means being of a type having an electrical resistance that increases upon increases of temperature above a predetermined temperature to limit the maximum operating temperature of the heater means, power supply leads in electrical circuit-forming relation with said heater means and extending from said heater means to the exterior of said casing for connection to a source of power, the surface of each end wall and the associated heat sink element disposed thereagainst being of similar arcuate configuration for conformable engagement to provide intimate surface-to-surface contact between each heat sink element and its associated end wall.

2. A contact lens disinfector according to claim 1 in which said surface of each end wall and its associated heat sink element is of substantially spherical configuration.

3. A contact lens disinfector according to claim 2 in which each end wall is of substantially spherical shape.

4. A contact lens disinfector according to claim 1 in which said heat sink elements are electrically conductive and there is an insulator between said heat sink elements.

5. A contact lens disinfector comprising: a casing formed from an electrically insulative material and defining a pair of wells at opposite ends thereof and opening in opposite directions for receiving contact lenses and a quantity of disinfecting solution, and removable cover means overlying the associated well opening, each said well having an end wall, which end walls included a convexed spherical surface opposite the well and said wells cooperate to define an interior cavity; a heater assembly disposed in said cavity and comprising a pair of metallic heat sink elements having a spherically concaved surface disposed against an associated end wall in intimate surface-to-surface contact therewith, electrical heater means intermediate and in surface-to-surface contact with said heat sink elements for supplying heat in opposite directions to each heat sink element and from the heat sink elements to the wells.

6. A contact lens disinfector according to claim 5, wherein said electrical heater means is of a type having an electrical resistance that increases rapidly once a predetermined temperature is reached thereby to limit the maximum operating temperature of said heater assembly.

7. A contact lens disinfector according to claim 6 wherein said heater assembly further includes a pair of disc shaped contacts on opposite sides of said electrical heater means and in electrical circuit forming relation with said heater means, said disc shaped contacts being interposed between said electrical heater means and said metallic heat sink elements.

8. A contact lens disinfector according to claim 7, wherein each said disc shape contact includes a terminal, power supply leads connected to said terminals and extending to the exterior of the casing.

9. A contact lens disinfector according to claim 8, further including an insulation member disposed within said casing, said insulating member including an aperture in which electrical heater means is disposed, and flange means serving to insulate said disc shaped contacts, said terminals and said power supply leads.

10. A contact lens disinfector comprising: a multi-part casing formed of an electrically insulative material and defining a pair of wells at opposite ends thereof and opening in opposite directions for receiving contact lenses and a quantity of disinfecting solution, each well opening to an end surface of the casing, and removable cover means overlying the associated well opening, each said well having an end wall opposite to said end surface, heater assembly means for supplying heat to said wells and comprising: a pair of metallic heat sink elements in said casing, and positioned exteriorly of said wells and each heat sink element having a surface disposed against an associated end wall in intimate surface-to-surface contact therewith, electrical heater means intermediate said heat sink elements for supplying heat in opposite directions to each heat sink element, electrical contact means associated with said heater means and being in electrical circuit-forming relation with said heater means, and power supply leads connected to said contact means and extending therefrom to the exterior of said casing for connection to a source of power, with said two piece casing serving to maintain the components of said heat generating means in assembly, while ensuring that the respective components are further maintained in both heat conductive and electrically conductive engagement as required.

11. A contact lens disinfector according to claim 10, wherein said electrical contact means is provided by a pair of plate like members in conductive contact with said electrical heater means, and said disinfector further including insulator means having a portion thereof disposed between the locations of engagement of the power supply leads with the respective plate like members providing said electrical contact means.

* * * * *